United States Patent
Banerjee et al.

(10) Patent No.: US 9,319,812 B2
(45) Date of Patent: Apr. 19, 2016

(54) SYSTEM AND METHODS OF SUBJECT CLASSIFICATION BASED ON ASSESSED HEARING CAPABILITIES

(75) Inventors: Bonny Banerjee, Palm Bay, FL (US); Lee Stanley Krause, Indialantic, FL (US); Alice Holmes, Gainesville, FL (US); Rahul Shrivastav, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1312 days.

(21) Appl. No.: 12/201,598

(22) Filed: Aug. 29, 2008

(65) Prior Publication Data

US 2010/0056951 A1 Mar. 4, 2010

(51) Int. Cl.
*A61B 5/12* (2006.01)
*H04R 25/00* (2006.01)
*A61B 5/00* (2006.01)

(52) U.S. Cl.
CPC ............... *H04R 25/70* (2013.01); *A61B 5/121* (2013.01); *A61B 5/7264* (2013.01); *H04R 2225/43* (2013.01); *H04R 2225/55* (2013.01)

(58) Field of Classification Search
CPC ......... A61B 5/121; A61B 5/123; H04R 25/70
USPC .............. 73/585; 381/329, 60; 600/559
See application file for complete search history.

(56) References Cited

U.S. PATENT DOCUMENTS

| | | | |
|---|---|---|---|
| 4,049,930 A | 9/1977 | Fletcher et al. | |
| 4,327,252 A | 4/1982 | Tomatis | |
| 4,953,112 A | 8/1990 | Widin et al. | |
| 5,008,942 A | 4/1991 | Kikuchi | |
| 5,606,620 A * | 2/1997 | Weinfurtner | 381/60 |
| 5,785,661 A | 7/1998 | Shennib | |
| 6,035,046 A | 3/2000 | Cheng et al. | |
| 6,036,496 A | 3/2000 | Miller et al. | |
| 6,118,877 A | 9/2000 | Lindemann et al. | |
| 6,446,038 B1 | 9/2002 | Bayya et al. | |
| 6,684,063 B2 | 1/2004 | Berger et al. | |
| 6,763,329 B2 | 7/2004 | Brandel et al. | |

(Continued)

FOREIGN PATENT DOCUMENTS

| | | |
|---|---|---|
| EP | 1519625 | 3/2005 |
| JP | 2002-291062 | 10/2002 |

(Continued)

OTHER PUBLICATIONS

Fujisaki et al. "Auditory Perception of Duration of Speech and Non-Speech Stimuli," 1973, pp. 45-64.

(Continued)

*Primary Examiner* — Lee S Cohen
*Assistant Examiner* — Emily Lloyd
(74) *Attorney, Agent, or Firm* — Merchant & Gould P.C.

(57) ABSTRACT

A method of assessing hearing characteristics of a subject is provided. The method includes determining a hearing capability of the subject based on responses of the subject to a series of sounds presented to the subject. Each sound corresponds to a presence, absence or irrelevance of a predetermined plurality of features. The method further includes assigning the subject to one of a predetermined plurality of classes based upon the responses of the subject, each of the plurality of classes being derived from hearing tests performed on a plurality of other subjects.

23 Claims, 4 Drawing Sheets

(56) References Cited

U.S. PATENT DOCUMENTS

| | | |
|---|---|---|
| 6,823,171 B1 | 11/2004 | Kaario |
| 6,823,312 B2 | 11/2004 | Mittal et al. |
| 6,913,578 B2 | 7/2005 | Hou |
| 6,914,996 B2 | 7/2005 | Takeda |
| 7,206,416 B2 | 4/2007 | Krause et al. |
| 7,236,573 B2 | 6/2007 | Bachorik et al. |
| 2002/0120440 A1 | 8/2002 | Zhang |
| 2002/0138272 A1 | 9/2002 | Bennett et al. |
| 2003/0007647 A1 | 1/2003 | Nielsen et al. |
| 2007/0286350 A1 | 12/2007 | Krause et al. |

FOREIGN PATENT DOCUMENTS

| | | |
|---|---|---|
| WO | WO-98/44762 | 10/1998 |
| WO | WO-99/31937 | 6/1999 |
| WO | WO-01/84538 | 11/2001 |
| WO | WO-2004/080532 | 9/2004 |
| WO | WO-2005/062766 | 7/2005 |
| WO | WO-2007/030402 | 3/2007 |
| WO | WO-2008/081446 | 7/2008 |

OTHER PUBLICATIONS

Runkle et al. "Active Sensory Tuning for Immersive Spatialized Audio," ICAD, 2000, 4 pages.
International Search Report for PCT Appl. No. PCT/US04/19843, mailed Mar. 22, 2006, 2 pages.
Written Opinion for PCT Appl. No. PCT/US04/19843, mailed Mar. 22, 2006, 5 pages.
Examination Report for European Patent Appl. No. 04755788.9, mailed Nov. 18, 2009, 4 pages.
International Search Report for PCT Appl. No. PCT/US09/55348, mailed Apr. 23, 2010, 5 pages.
Written Opinion for PCT Appl. No. PCT/US09/55348, mailed Apr. 23, 2010, 10 pages.
International Search Report for PCT Appl. No. PCT/US2010/029020, mailed Jul. 12, 2010, 3 pages.
Written Opinion for PCT Appl. No. PCT/US2010/029020, mailed Jul. 12, 2010, 7 pages.
International Search Report for PCT Appl. No. PCT/US2010/029021, mailed Jul. 16, 2010, 3 pages.
Written Opinion for PCT Appl. No. PCT/US2010/029021, mailed Jul. 16, 2010, 7 pages.

* cited by examiner

SYSTEM AND METHODS OF SUBJECT CLASSIFICATION BASED ON ASSESSED HEARING CAPABILITIES

FIELD OF THE INVENTION

The present invention is related to the field of hearing testing, and more particularly, to techniques for more efficiently assessing hearing capabilities and tuning hearing-enhancement and audio devices.

BACKGROUND OF THE INVENTION

Tuning a hearing-enhancement device to fit a particular subject is typically costly and time consuming, both for a hearing-impaired subject and an audiologist. Using conventional techniques, it is often extremely difficult for the audiologist to manually tune the large number of parameters that usually must be set if the hearing-enhancement device is to perform optimally. As a result, even after considerable expenditure of time and money, a subject may not benefit from a hearing-enhancement device or system.

Typical of difficulties inherent in tuning a digital hearing device are the difficulties often encountered in tuning a cochlear implant. Once such a system is implanted, as with many other types of digital hearing-enhancement systems, a suitable speech coding and mapping strategy must be selected to optimize the performance of the system for day-to-day operation. The mapping strategy pertains to an adjustment of parameters corresponding to one or more independent channels of a multi-channel cochlear implant or other hearing-enhancement system. Selection of a strategy typically occurs over an introductory period of approximately six or seven weeks, during which the hearing-enhancement system is tuned for the particular subject. During this tuning period, users of such systems are asked to provide feedback on how they feel the device is performing.

More particularly, to create a mapping for a speech processor, an audiologist first determines the electrical dynamic range for each electrode or sensor used. The programming system delivers an electrical current through the hearing-enhancement system to each electrode in order to obtain the electrical threshold (T-level) and comfort or "max" level (C-level) measures defined by a system's manufacturer. T-level or minimum stimulation level is the softest electrical current capable of producing an auditory sensation in the subject 100 percent of the time. The C-level is the loudest level of signal to which a subject can listen comfortably for a long period of time.

A speech processor is then programmed or "mapped" using one of several encoding strategies so that the electrical current delivered to the implant will be within this measured dynamic range, i.e., between the T- and C-levels. After T- and C-levels are established and the mapping is created, the microphone is activated so that the subject is able to hear speech and other sounds. From that point onwards the tuning process continues as a traditional hearing test. Hearing-enhancement device users are asked to listen to tones of varying frequencies and amplitudes. The gain of each channel can be further altered within the established threshold ranges such that the subject is able to hear various tones of varying amplitudes and frequencies reasonably well.

Thus, as already noted, fitting and tuning a hearing-enhancement system of any type so as to meet the needs of a particular subject is typically quite costly and very time consuming, both from the perspective of the hearing-impaired subject and the audiologist. The functions of such a system are regulated by a large number of parameters, values for each of which must be determined so as to tune the system to provide optimal performance for the particular subject. In order to do so, the subject has to be thoroughly tested with respect to each set of parameter values. The number of tests increases exponentially as the number of system parameters increases.

SUMMARY OF THE INVENTION

In view of the foregoing background, it is thus an aspect of the invention to provide systems and methods for effective and efficient tuning of an audio device, such as a digital hearing-enhancement device, for a particular subject. An aspect of the invention is the utilization of knowledge obtained through previous testing of similar subjects so as to identify suggested parameter values in tuning the audio device.

One embodiment of the invention is a system for tuning a hearing-enhancement device. The system can include a subject interface for rendering a series of sounds to a subject and for receiving from the subject a response to each of the sounds rendered, each sound corresponding to one or more features belonging to a predetermined plurality of features. The system further can include a processing unit communicatively linked to the subject interface. The processing unit can include a hearing-capability module for determining a hearing capability of the subject based on the received responses of the subject to the series of sounds rendered. Additionally, the processing unit can include a. class-assigning module for assigning the subject to one of a predetermined plurality of classes based upon the received responses, each of the plurality of classes being derived from hearing tests performed on a plurality of other subjects. The processing unit can further include a tuning module for setting one or more parameters of a hearing-enhancement device based on the class to which the subject is assigned.

Another embodiment of the invention is a method of assessing hearing characteristics of a subject. The method can include determining a hearing capability of the subject based on responses of the subject to a series of sounds presented to the subject, each sound corresponding to a presence, absence or irrelevance of a predetermined plurality of features. The method also can include assigning the subject to one of a predetermined plurality of classes based upon the responses of the subject, each of the plurality of classes being derived from hearing tests performed on a plurality of other subjects.

Still another embodiment of the invention is a computer-readable storage medium in which computer-readable code is embedded. The computer-readable code can be configured to cause a computing system to perform the following steps when loaded on and executed by the computing system: determine a hearing capability of a subject based on responses of the subject to a series of sounds presented to the subject, each sound corresponding to a presence, absence or irrelevance of a predetermined plurality of features, and assign the subject to one of a predetermined plurality of classes based on his responses, each of the plurality of classes being derived from hearing tests performed on a plurality of other subjects.

BRIEF DESCRIPTION OF THE DRAWINGS

There are shown in the drawings, embodiments, which are presently preferred. It is expressly noted, however, that the invention is not limited to the precise arrangements and instrumentalities shown in the drawings.

DETAILED DESCRIPTION

Figure 1:
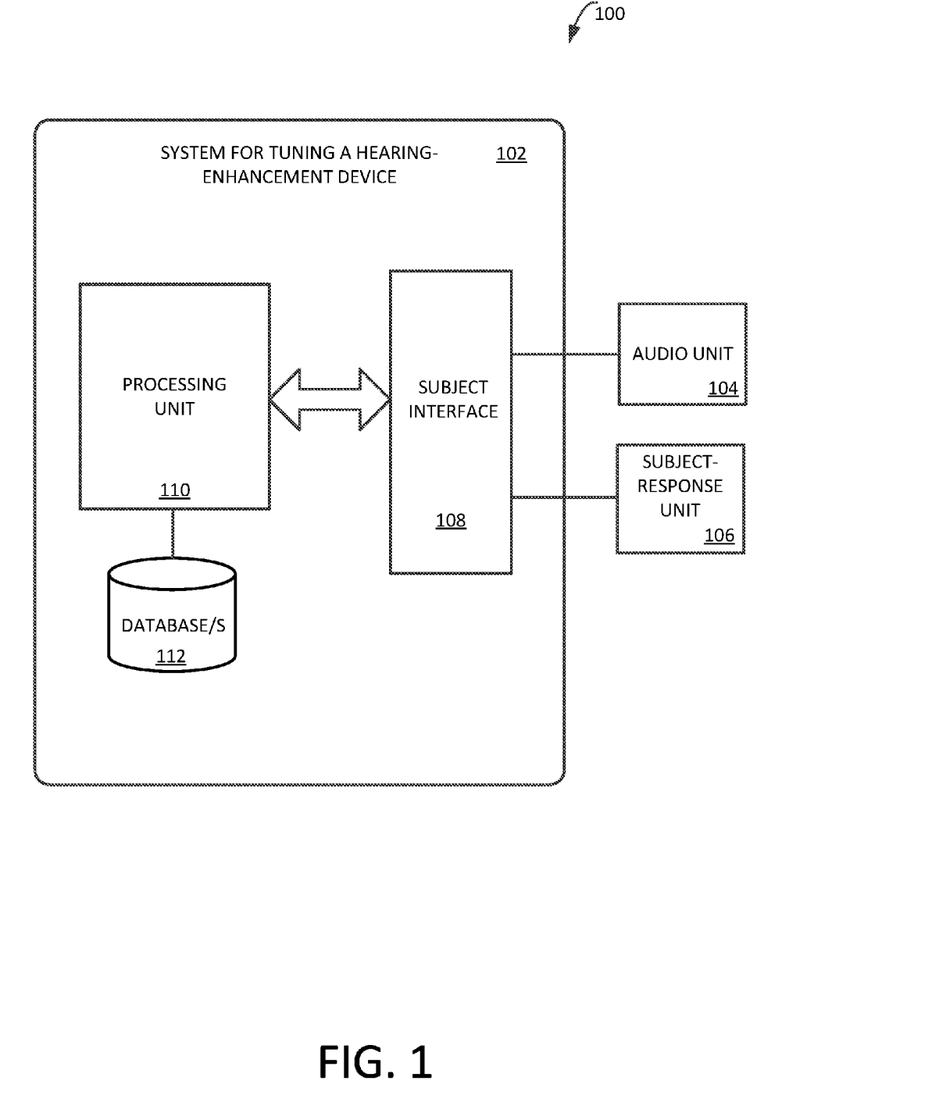
FIG. 1 is a schematic diagram of an environment in which a system for tuning a hearing-enhancement device, according to one embodiment of the invention, can be utilized.

FIG. 1 is a schematic view of an exemplary environment 100 in which system 102 for tuning a hearing-enhancement device, according to one embodiment, can be utilized. The exemplary environment 100 illustratively comprises, in addition to the system 102, an audio unit 104 that delivers sound signals to the system. The audio unit 104 can comprise, for example, a speaker, headphones, or other electromechanical transducer (not explicitly shown) for generating sound signals in response to electrical signals that can be conveyed from the system 102 to the audio unit, the sounds being rendered then to a user of the audio unit. Indeed, in a particular embodiment, the audio unit 104 can be the hearing-enhancement device that is to be tuned. In an alternative embodiment, however, the hearing-enhancement device can be a separate device that also connects to the system 102.

The audio unit 104 can optionally include a microphone or other acoustical transducer for converting acoustic signals generated by the subject of the audio unit 104 into electrical signals that are conveyed to the system. The exemplary environment 100 might additionally or alternately include a separate subject-response unit 106, such as a computer terminal for presenting a graphical of other subject interface with which a subject interacts using a keyboard and/or computer mouse (neither explicitly shown). The purpose of these different arrangements, as described more particularly below, is to permit the system 102 to present to the subject a series of sounds to which the subject responds so as to assess hearing capabilities of the subject.

According to a particular embodiment, the system 102 includes a subject interface 108 configured to communicatively link the system to the audio unit 104. If the exemplary environment 100 additionally or alternatively includes separate subject-response unit 106, then the subject interface 108 (or a corresponding one) also can be configured to communicatively link the system 102 to the subject-response unit. Thus, the subject interface 108 can be used in playing the series of sounds that are presented to the subject to a subject and for receiving, from the subject a response to each of the sounds played. Each such sound, as described more particularly below, corresponds to the presence, absence or irrelevance of a predetermined plurality of features. Illustratively, the system 102 further includes a processing unit 110 for effecting the operative processes, procedures, and functions that are described more particularly below.

Optionally, the system 102 can also include one or more databases 112 for storing the plurality of features and/or sound signals, such as phonemes, words, etc., that correspond to the presence, absence or irrelevance of the plurality of features. Although, the system 102 is shown as communicatively linked directly, wirelessly or through a wire-line connection, with the audio unit 104, it will be readily apparent to one skilled in the relevant art that the system can be communicatively linked to the audio unit through one or more intermediate nodes.

Figure 2:
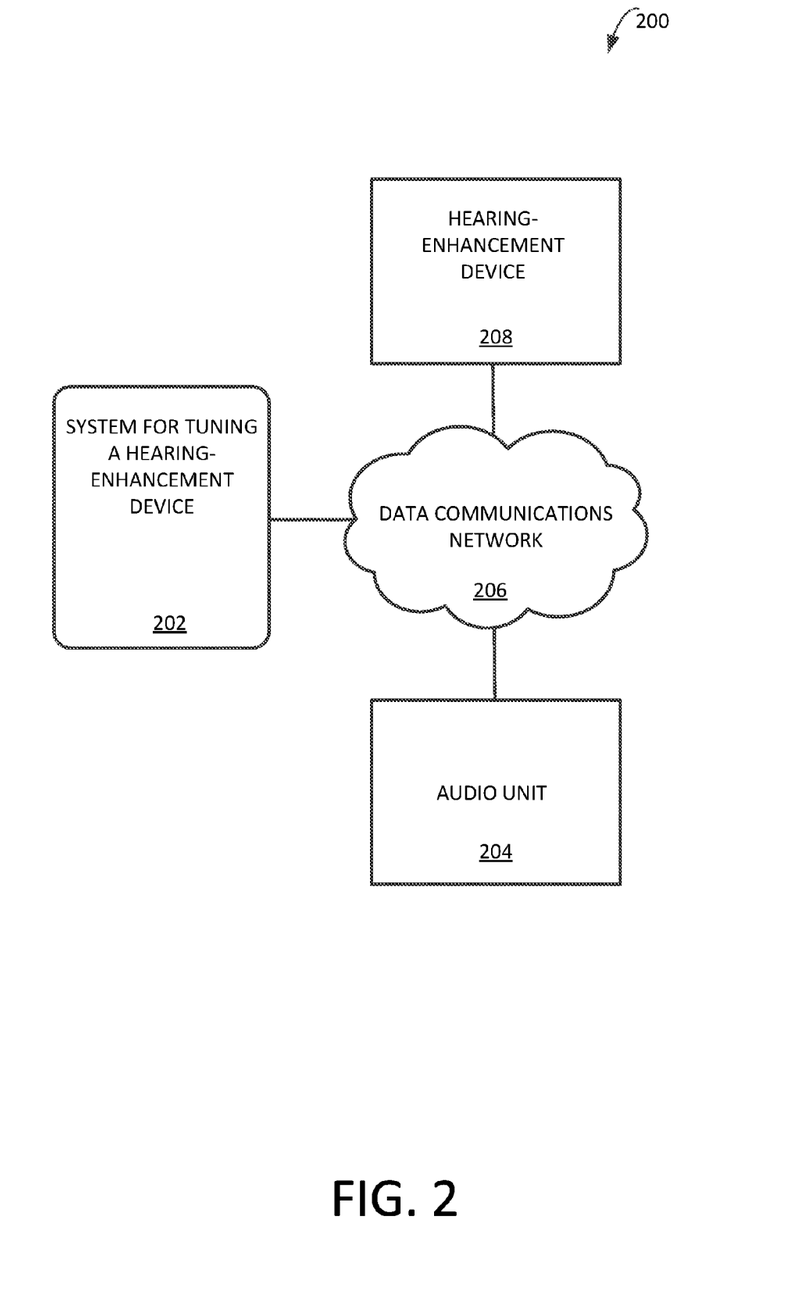
FIG. 2 is a schematic diagram of another environment in which a system for tuning a hearing-enhancement device, according to a different embodiment of the invention, can be utilized.

FIG. 2 illustrates one such embodiment in which a system 202 for tuning a hearing-enhancement device is linked to an audio unit 204 through a data communications network 206, such as a local-area network (LAN), a wide-area network (WAN), or a plurality of connected networks such as the Internet. Alternatively or additionally, the system 202 and audio unit 204 can be communicatively linked through a public-switched telephony network. As already noted above, a hearing-enhancement device being tuned can also serve as the audio unit that connects to the system, or alternatively, the hearing-enhancement device and audio unit can be separate devices. Thus, as illustrated with this embodiment, the system 202 can optionally connect separately to the audio unit 204 and to a hearing-enhancement device that is tuned by the system through the same network 206 or even a separate one.

Figure 3:
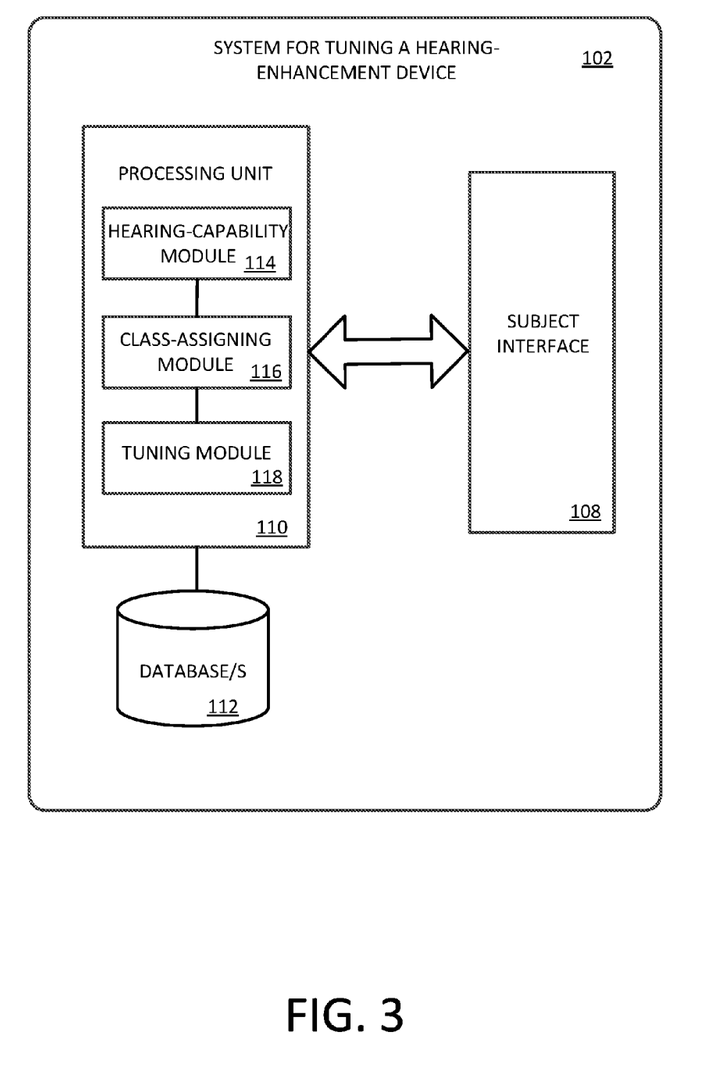
FIG. 3 is a more detailed schematic view of a system for tuning a hearing-enhancement device, according to one embodiment of the invention.

Referring now to FIG. 3, a more detailed schematic view is provided of the system 102, according to a particular embodiment. According to this embodiment, the processing unit 110 of the system 102 includes a hearing-capability module 114. The system 102, according to this embodiment, further illustratively includes a class-assigning module 116 communicatively linked to the hearing-capability module 114. Additionally the system illustratively includes a tuning module 118. One or more of the hearing-capability module 114, class-assigning module 116, and a tuning module 118 can be implemented in a combination of logic-based circuitry and processor-executable code. Thus; the processing unit 110 can be a general-purpose computer or application-specific computer having one or more processors implemented with registers, arithmetic-logic units, control units, and/or other logic-based circuitry. Alternatively, one or more of the hearing-capability module 114, class-assigning module 116, and a tuning module 118 can be implemented in dedicated, hardwired circuitry configured to operate cooperatively with other elements of the system 102.

Operatively, the subject interface 108 plays a series of sounds to the subject and, in response thereto, receives from the subject a response to each of the sounds played. Each sound, as already noted, corresponds to the presence, absence or irrelevance of a predetermined plurality of features. The hearing-capability module 114 of the processing unit 110 determines a hearing capability of the subject based on the received responses to the series of sounds played. The class-assigning module 116 assigns the subject to one of a predetermined plurality of classes based upon the received responses. Each of the plurality of classes consists of none, one or more subjects based on their hearing characteristics as assessed from the hearing tests performed on them. The tuning module 118 operates by setting one or more parameters of the hearing-enhancement device based on the device parameter settings of a similar subject in the class to which the subject is assigned.

In a preferred embodiment, the series of sounds presented by the system 102 to the subject are phonemes. Thus, during testing, a series of phonemes are presented and after each presentment the subject responds, either audibly or using a subject-response unit as described above. Optionally, the system 102 can include a recording device (not shown) to record not only the subject's response but the response time of the subject. Based on the responses, the system 102 can incrementally build a model from which the strengths and weaknesses of the subject can be determined. This knowledge, in turn, can be used to determine parameter values for tuning the particular hearing-enhancement device, so that it performs at or sufficiently near to an optimal level.

It is known that in natural language, a phoneme is the smallest unit of speech that distinguishes meaning. Words and sentences are a combination of phonemes in a particular order. According to a preferred embodiment, the system 102 is configured to present to the subject phonemes selected from a set of fourteen consonant phonemes (as distinct from words or sentences), the phonemes being those identified in the Iowa Medial Consonant Recognition Test. Vowel phonemes need not be utilized by the system, primarily because such are considered too easy to perceive and thus much less likely to be useful indicators of the nature of hearing capabilities or hearing loss.

As described, the system 102 thus provides an analysis of the subject's strengths and weaknesses in terms of a predetermined set of features associated with each phoneme. Particularly, a. phoneme can be characterized by the presence, absence, or irrelevance of a set of nine features: Vocalic, Consonantal, Compact, Grave, Flat, Nasal, Tense, Continuant, and Strident. (See, e.g., R. Jakobson, G. Fant, and M. Halle, PRELIMINARIES OF SPEECH ANALYSIS, Cambridge, Mass.: MIT Press (1963), incorporated herein in its entirety.) The features can be arranged hierarchically such that errors in recognizing a feature "higher" in the hierarchy result in more extensive speech-recognition problems, because a feature higher in the hierarchy affects a greater number of phonemes. As shown in U.S. Pat. No. 7,206,416 to Krause, et al., these features provide a more comprehensive measure of the subject's nature of hearing loss as compared to words or sentences. With each phoneme is associated a percentage of proportional occurrence in the English language. (See, e.g., L. Shriberg and R. Kent, Clinical Phonetics, Boston: Allyn & Bacon (2003), incorporated here in its entirety.)

The presence, absence, and irrelevance of a feature can be represented by a 1, −1, and 0, respectively. Accordingly, the fourteen consonant phonemes from the Iowa Medical Consonant Recognition Test and their constituent features are as follows:

that the optimum parameters values for one of the subjects are the same or very nearly so for the other. Using knowledge obtained from previously-tested subjects can thus contribute significantly to the goal of improving the effectiveness and efficiency of testing a subject and setting parameter values by suggesting those values most likely to be the optimal settings. Utilizing the suggested parameter values can reduce testing and tuning times significantly.

A subject's performance in a test can be measured by the number of phonemes that the subject fails to perceive correctly. This, however, fails to capture the subject's strengths and weaknesses because many phonemes share similar features. For example, the phonemes 'f' and 'p' differ only in one out of the nine features called Continuant. A person who fails to perceive 'p' due to an error in any feature other than Continuant will likely fail to perceive 'f' as well. The converse is also true. Thus counting the number of phoneme errors is likely to be meaningless because feature errors give rise to phoneme errors. For the same reason, in order to reduce the phoneme errors, the system 102 is configured to concentrate instead on feature errors.

According to one embodiment, the hearing-capability module 114 is configured to determine hearing capability of the subject by identifying one or more of the plurality of features as contributing more than the others to a failure of the subject to correctly respond to the presentment of one or more of the series of sounds. More particularly, the hearing-capability module 114 can be configured to treat a failure to correctly respond to a particular one of the series of sounds as a feature error. Each feature error corresponds to a particular one of the series of sounds, which preferably are each phonemes.

Accordingly, the hearing-capability module 114 can be further configured to measure the hearing performance of the

| Phonemes | Vocalic | Cons. | Compact | Grave | Flat | Nasal | Tense | Cont. | Strident |
|---|---|---|---|---|---|---|---|---|---|
| n  | −1 | 1 | −1 | −1 | 0 | 1  | 0  | 0  | 0  |
| t  | −1 | 1 | −1 | −1 | 0 | −1 | 1  | −1 | 0  |
| s  | −1 | 1 | −1 | −1 | 0 | −1 | 1  | 1  | 1  |
| d  | −1 | 1 | −1 | −1 | 0 | −1 | −1 | −1 | 0  |
| k  | −1 | 1 | −1 | 0  | 0 | −1 | 1  | −1 | −1 |
| m  | −1 | 1 | −1 | 1  | 0 | 1  | 0  | 0  | 0  |
| z  | −1 | 1 | −1 | −1 | 0 | −1 | −1 | 1  | 1  |
| b  | −1 | 1 | −1 | 1  | 0 | −1 | −1 | −1 | 0  |
| p  | −1 | 1 | −1 | 1  | 0 | −1 | 1  | −1 | 0  |
| v  | −1 | 1 | −1 | 1  | 0 | −1 | −1 | 1  | 0  |
| f  | −1 | 1 | −1 | 1  | 0 | −1 | 1  | 1  | 0  |
| g  | −1 | 1 | 1  | 0  | 0 | −1 | −1 | −1 | −1 |
| sh | −1 | 1 | 1  | 0  | 0 | −1 | 1  | 1  | 0  |
| j  | −1 | 1 | 1  | 0  | 0 | −1 | −1 | −1 | 1  |

The features Vocalic and Consonantal remain the same with respect to all fourteen phonemes. The features Tense, Continuant, and Strident do not make a substantial difference to hearing ability, as has been verified empirically. Moreover, the feature Flat does not influence any of the fourteen phonemes. Thus, in a preferred embodiment, the system 102 is configured to classify subjects based on their performance in the three features: Compact, Grave, and Nasal.

An objective of the system 102 is to significantly reduce resource expenditures and time in testing. One way to achieve this is by using knowledge obtained through testing of other subjects or subjects in the past. The knowledge can be used to suggest parameter values for tuning a hearing-enhancement device for a particular subject. Two subjects often have similar hearing characteristics, in which case it is highly probable subject based on a computed mean of feature errors. Specifically, the computed mean of feature errors can be a weighted mean, and the hearing-capability module 114 can be configured to compute the weighted mean, $\xi$, to be equal to $$\xi = \frac{\sum_{i=1}^{N} w_i n_i}{\sum_{i=1}^{N} w_i}$$

where $w_i$ is a weight assigned to the $i^{th}$ feature of the plurality of features and $n_i$ is the number of feature errors with respect to the $i^{th}$ feature.

An experimentally-determined set of weights for the nine above-listed features—Vocalic, Consonantal, Compact, Grave, Flat, Nasal, Tense, Continuant, and Strident—is {0.151785714, 0.151785714, 0.098214286, 0.0, 0.142857143, 0.125, 0.125, 0.0625}.

The system 102 can classify a subject based on the subject's strengths and weaknesses in perceiving phonemes. The objective is to classify subjects with similar hearing characteristics in the same class and subjects with different hearing characteristics in different classes. Two subjects are considered to have similar hearing characteristics if the same feature contributes more errors than another feature. As already noted, only three features—Compact, Grave, and Nasal—contribute significantly in determining the nature of hearing loss for a majority of subjects. The weights assigned to these features from the experimentally determined set are 0.142857143, 0.098214286, and 0.142857143, respectively.

For each subject, the class-assigning module 116 can be configured to rank the three features based on their weighted contribution to the total weighted error. Thus for the $i^{th}$ feature, $f_i$, among the plurality of features, the class-assigning module 116 can be configured to compute the weighted contribution to be $$\text{Contribution}(f_i) = \frac{w_i n_i}{\xi}$$

wherein Contribution($f_i$) is the weighted contribution of the $i^{th}$ feature.

Based on the ranking of this particular three-element set of features, six classes are possible:
<Compact, Grave, Nasal>
<Compact, Nasal, Grave>
<Nasal, Compact, Grave>
<Grave, Compact, Nasal>
<Grave, Nasal, Compact>
<Nasal, Grave, Compact> where <X, Y, Z> denotes the weighted contribution of errors from the feature X is more than that of the feature Y, which is, in turn, more than that of the feature Z. Thus, for example, <Compact, Grave, Nasal> denotes the weighted contribution of errors from the feature Compact is more than that of the feature Grave, which is, in turn, more than that of the feature Nasal. Each of the other combinations similarly identifies which feature contributes more to error than do the others among the plurality of features.

A subject belongs to one of the six classes. It is noted that when testing begins initially, the class to which the subject belongs is unknown. After the first test, the subject's class can be determined but that might change after one or more additional tests. Once enough tests have been performed with different parameter values, the results clearly reveal the strengths and weaknesses of the subject.

Membership of two subjects in the same class suggests that the same features contribute the most and least to their hearing weaknesses. Since features constitute phonemes, it is expected that both subjects will have similar phoneme errors and hence close optimal parameter values for the same hearing-enhancement device. Knowing the successful parameter values of a subject from a class thus rapidly suggests a good set of parameter values for another subject belonging to the same class, which can be determined as soon as the other subject's class can be determined with some level of certainty, since both of their optimal performances occur at nearby locations in the respective models. Accordingly, subject classification can significantly improve the efficacy and efficiency of testing hearing and tuning a hearing-enhancement device.

Figure 4:
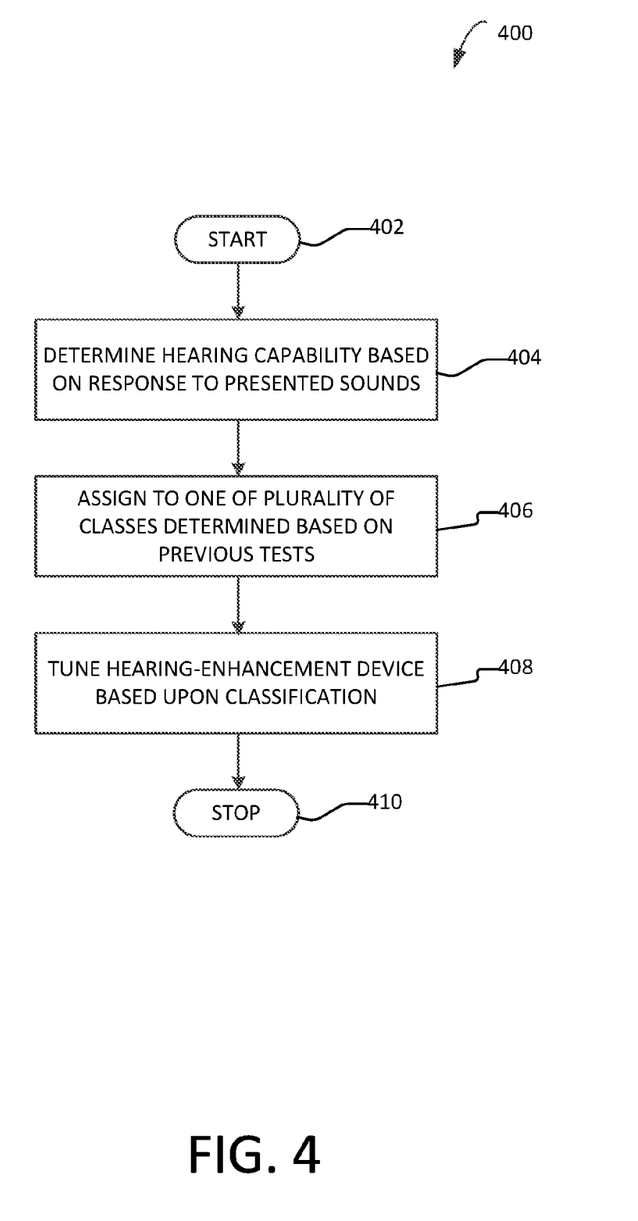
FIG. 4 is a flowchart of exemplary steps in a method of testing a hearing-impaired subject, according to still another embodiment of the invention.

Certain method aspects of the invention are illustrated in FIG. 4. FIG. 4 is a flowchart of exemplary steps in a method 400 of assessing hearing characteristics of a subject. The method can include, after the start at block 402, determining a hearing capability of the subject based on his responses to a series of sounds presented to him at block 404. Each sound corresponds to the presence, absence or irrelevance of a predetermined plurality of features. The method 400 continues at block 406 by assigning the subject to one of a predetermined plurality of classes based upon the responses of the subject. Each of the plurality of classes is derived from hearing tests performed on a plurality of other subjects. Optionally, the method 400 can include, at block 408, setting one or more parameters of a hearing-enhancement device based on the class to which the subject is assigned. The method 400 illustratively concludes at block 410.

According to one embodiment of the method 400, the step of determining hearing capability of a subject at block 404 can include identifying one or more of the plurality of features as contributing more than other of the plurality of features to a failure of the subject to correctly respond to the presentment of one or more of the series of sounds. A failure to correctly respond to a particular one of the series of sounds, more particularly, can define a feature error with respect to the one or more features corresponding to that particular one of the series of sounds. Thus, the method 400 can further include measuring the performance of the subject based on a computed mean of feature errors.

The computed mean of feature errors can, moreover, equal a weighted mean, and the method can further comprise computing the weighted mean, $\xi$, to be equal to $$\xi = \frac{\sum_{i=1}^{N} w_i n_i}{\sum_{i=1}^{N} w_i}$$

where $w_i$, is a weight assigned to the $i^{th}$ feature of the plurality of features and $n_i$ is the number of feature errors with respect to the $i^{th}$ feature.

According to still another embodiment, the step of assigning the subject to one of the predetermined plurality of classes at block 406 can include computing a weighted contribution of each feature. The weighted contribution of a feature can quantitatively measure the contribution that the feature makes to the computed mean of feature errors. Moreover, computing the weighted contribution of a feature can comprise computing a value equal to $$\text{Contribution}(f_i) = \frac{w_i n_i}{\xi}$$

wherein Contribution($f_i$) is the weighted contribution of the $i^{th}$ feature.

The invention, as also already noted, can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The foregoing description of preferred embodiments of the invention has been presented for the purposes of illustration. The description is not intended to limit the invention to the precise forms disclosed. Indeed, modifications and variations will be readily apparent from the foregoing description. Accordingly, it is intended that the scope of the invention not be limited by the detailed description provided herein.

The invention claimed is:

1. A computer implemented method of assessing hearing characteristics of a person, the method comprising:
providing, by a processor, a series of sounds to an interface configured to present the series of sounds to a person, wherein different sounds in the series of sounds corresponding to at least one of a presence, absence or irrelevance of a predetermined plurality of consonant features, wherein the predetermined plurality of consonant features comprises at least a Nasal feature, a Compact feature, and a Grave feature;
determining, by the processor, a hearing capability of the person based on responses of the person to the series of sounds; and
assigning, by the processor, the person to one of a predetermined plurality of classes based upon the responses of the person, each of the plurality of classes describing errors made primarily with respect to the Nasal, Compact, and Grave consonant features.

2. The method of claim 1, further comprising setting, by the processor, one or more parameter values of a hearing-enhancement device based on the class to which the person is assigned.

3. The method of claim 1, wherein determining the hearing capability comprises identifying one or more of the predetermined plurality of consonant features as contributing more than other consonant features of the predetermined plurality of consonant features to one or more failures to correctly respond to one or more sounds of the series of sounds.

4. The method of claim 3, wherein the one or more failures to correctly respond to the one or more sounds of the series of sounds defines one or more feature errors made with respect to the one or more features corresponding to the one or more sounds of the series of sounds, and further comprising generating a performance measure for the person based upon a computed mean of the one or more feature errors.

5. The method of claim 4, wherein the computed mean of the one or more feature errors equals a weighted mean, and further comprising computing the weighted mean, $\xi$, to be equal to $$\xi = \frac{\sum_{i=1}^{N} w_i n_i}{\sum_{i=1}^{N} w_i}$$

where $w_i$ is a weight assigned to the $i^{th}$ feature of the predetermined plurality of consonant features and $n_i$ is the number of feature errors with respect to the $i^{th}$ feature.

6. The method of claim 5, wherein the assigning the person to one of the predetermined plurality of classes comprises computing a weighted contribution of each feature, the weighted contribution of a feature quantitatively measuring the contribution that each feature makes to the computed mean of feature errors.

7. The method of claim 6, wherein computing the weighted contribution of each feature comprises computing a value equal to $$\text{Contribution}(f_i) = \frac{w_i n_i}{\xi}$$

wherein Contribution($f_i$) is the weighted contribution of the $i^{th}$ feature.

8. The method of claim 1, wherein the plurality of classes describe the errors made by the assigned persons with respect to Nasal, Compact, and Grave consonant features and no other consonant features.

9. A system for tuning a hearing-enhancement device, the system comprising:
an interface for rendering a series of sounds to a person and for receiving from the person a response to each of the sounds rendered, different sounds of the series of sounds correspond to one or more features belonging to a predetermined plurality of consonant features, wherein the plurality of consonant features comprises at last a Nasal feature, a Compact feature, and a Grave feature; and
a processing unit communicatively linked to said interface, the processing unit configured to:
determine a hearing capability of the person based on the received responses of the person to the series of sounds rendered,
assign the person to one of a predetermined plurality of classes based upon received responses, each of the plurality of classes describing errors made by the person primarily with respect to the Nasal, Compact, and Grave consonant features, and
set one or more parameters of the hearing-enhancement device based on the class to which the person is assigned.

10. The system of claim 9, wherein determining the hearing capability of the person comprises identifying one or more of the predetermined plurality of consonant features as contributing more than other of the predetermined plurality of consonant features to one or more failures of the person to correctly respond to one or more sounds of the series of sounds.

11. The system of claim 10, wherein the one or more failures to correctly respond to the one or more sounds of the series of sounds defines one or more feature errors made with respect to the one or more features corresponding to the one or more sounds of the series of sounds, and wherein the processing unit is further configured to measure a hearing performance of the person based on a computed mean of the one or more feature errors.

12. The system of claim 11, wherein the computed mean of the one or more feature errors equals a weighted mean, and wherein the processing unit is further configured to compute the weighted mean, $\xi$, to be equal to $$\xi = \frac{\sum_{i=1}^{N} w_i n_i}{\sum_{i=1}^{N} w_i}.$$

where $w_i$ is a weight assigned to the $i^{th}$ feature of the predetermined plurality of consonant features and $n_i$ is the number of feature errors with respect to the $i^{th}$ feature.

13. The system of claim 12, wherein the processing unit is further configured to assign the person to one of the predetermined plurality of classes by computing a weighted contribution of each feature, the weighted contribution of a feature quantitatively measuring the contribution that each feature makes to the computed mean of feature errors.

14. The system of claim 13, wherein the processing unit is further configured to compute the weighted contribution of each feature by determining a value equal to $$\text{Contribution}(f_i) = \frac{w_i n_i}{\xi}$$

wherein Contribution($f_i$) is the weighted contribution of the $i^{th}$ feature.

15. The system of claim 9, wherein the plurality of classes describe the errors made by the assigned persons with respect to Nasal, Compact, and Grave consonant features and no other consonant features.

16. A non-transitory computer-readable storage medium in which computer-readable instructions are embedded, the computer-readable instructions, when executed by a processing unit, cause the processing unit to perform a method comprising:
    providing, a series of sounds to an interface configured to present the series of sounds to a person, wherein different sounds in the series of sounds correspond to at least one of a presence, absence or irrelevance of a predetermined plurality of consonant features, wherein the predetermined plurality of consonant features comprises at least a Nasal feature, a Compact feature, and a Grave feature;
    determining a hearing capability of the person based on responses of the person to the series of sounds; and
    assigning the person to one of a predetermined plurality of classes based on the person's responses, each of the plurality of classes describing errors made by the person primarily with respect to the Nasal, Compact, and Grave consonant features.

17. The non-transitory computer-readable storage medium of claim 16, wherein the method further comprises setting one or more parameter values of a hearing-enhancement device based upon the class to which the person is assigned.

18. The non-transitory computer-readable storage medium of claim 16, wherein determining the hearing capability comprises identifying one or more of the predetermined plurality of consonant features as contributing more than other of the predetermined plurality of consonant features to one or more failures to correctly respond to one or more sounds of the series of sounds.

19. The non-transitory computer-readable storage medium of claim 18, wherein the one or more failures to correctly respond to the one or more sounds of the series of sounds identifies one or more feature errors made with respect to the one or more features corresponding to the one or more sounds of the series of sounds, and wherein the method comprises measuring a hearing performance of the person based on a computed mean of feature errors.

20. The non-transitory computer-readable storage medium of claim 19, wherein the computed mean of the one or more feature errors equals a weighted mean, and further comprising computing the weighted mean, $\xi$, to be equal to $$\xi = \frac{\sum_{i=1}^{N} w_i n_i}{\sum_{i=1}^{N} w_i}$$

where $w_i$ is a weight assigned to the $i^{th}$ feature of the plurality of features and $n_i$ is the number of feature errors with respect to the $i^{th}$ feature.

21. The non-transitory computer-readable storage medium of claim 20, wherein assigning the person to one of the predetermined plurality of classes comprises computing a weighted contribution of each feature, the weighted contribution of each feature quantitatively measuring the contribution that each feature makes to the computed mean of feature errors.

22. The non-transitory computer-readable storage medium of claim 21, wherein computing the weighted contribution of each feature comprises computing a value equal to $$\text{Contribution}(f_i) = \frac{w_i n_i}{\xi}$$

wherein Contribution($f_i$) is the weighted contribution of the $i^{th}$ feature.

23. The non-transitory computer-readable storage medium of claim 16, wherein the plurality of classes describe the errors made by the assigned persons with respect to Nasal, Compact, and Grave consonant features and no other consonant features.

* * * * *